ic Patent [19]

Eisenbrand

[11] 4,228,086
[45] Oct. 14, 1980

[54] N-SUBSTITUTED ALKYL-N-NITROSOCARBAMOYL AZIDES

[76] Inventor: Gerhard Eisenbrand, Banngartenstrasse 19, 6902 Sandhausen, Fed. Rep. of Germany

[21] Appl. No.: 22,714

[22] Filed: Mar. 21, 1979

Related U.S. Application Data

[62] Division of Ser. No. 800,452, May 25, 1977, Pat. No. 4,150,146.

[30] Foreign Application Priority Data

May 25, 1976 [DE] Fed. Rep. of Germany ....... 2623420

[51] Int. Cl.² ............................................ C07C 117/00
[52] U.S. Cl. ....................................................... 260/349
[58] Field of Search ......................................... 260/349

[56] References Cited

U.S. PATENT DOCUMENTS 4,150,146  4/1979  Eisenbrand .................. 260/349 X

FOREIGN PATENT DOCUMENTS 2623420 10/1977 Fed. Rep. of Germany ...... 260/349 X 2659862  3/1978 Fed. Rep. of Germany ... 260/349 OR

OTHER PUBLICATIONS

Chemical Abstracts, vol. 88, abst. 37285q (1978) (abst. of Ger. Offen. 2,623,420).
Chemical Abstracts, vol. 88, abst. 190,126h (1978) (abst. of Ger. Offen. 2,659,862).
Oliveri–Mandala et al., Chem. Abstracts, vol. 7, p. 3495 (1913).
Beilsteins Handbuch Der Organischen Chemie, vol. 3, Erstes Erganzungswerk, system No. 210, pp. 59–60, Verlag von Julius Springer, Berlin, Germany (1929).

*Primary Examiner*—John D. Randolph
*Attorney, Agent, or Firm*—Michael Klotz

[57] ABSTRACT

The invention relates to the preparation of novel N-substituted alkyl-N-nitrosocarbamoyl azides and to the compounds obtained thereby. The novel N-substituted alkyl-N-nitrosocarbamoyl azides can be reacted with amines, diamines, aminoalcohols, aminoacids or aminoacid derivatives to prepare unsymmetrically 1,3-disubstituted nitrosoureas which show therapeutical activity.

8 Claims, No Drawings

N-SUBSTITUTED ALKYL-N-NITROSOCARBAMOYL AZIDES

This is a division of Ser. No. 800,452 filed May 25, 1977 now U.S. Pat. No. 4,150,146, issued on Apr. 17, 1979.

The present invention relates to new intermediate compounds for the preparation of unsymmetrically 1,3-disubstituted nitroso ureas.

Specific 1-(2-chloroethyl)-1-nitroso ureas, particularly 1,3-bis-(2-chloroethyl)-1-nitroso urea (BCNU), have been used as chemotherapeutic agent for the treatment of a number of experimental and clinical tumors (Adv. in Cancer Res., 16,237 to 332, 1972). A number of studies have been made of the working mechanism and the chemotherapeutic activity of such compounds, leading to the conclusion that the observed toxicity of the compounds is probably mostly influenced by the carbamoylating activity of the decomposition products (Wheeler et al., Cancer Res., 34, 194 to 200, 1974). However, the biological effects of the alkylating and carbamoylating agents, obtained by the breakdown of the nucleus in vivo and in vitro, are little known.

There is therefore the greatest need to prepare the analogs of the known nitroso ureas in order to modify their chemotherapeutic activity, particularly the toxicity and the anti-tumor activity, as well as their solubility in water or in tissue fluids.

It is an object of the invention to discover novel intermediate compounds from which the new analogs of BCNU can be prepared.

These and other objects are achieved by the discovery of novel N-substituted alkyl-N-nitrosocarbamoyl azides from which the new unsymmetrically 1,3-disubstituted nitroso ureas can be made.

In the preparation of an unsymmetrical 1,3-disubstituted-nitroso urea, the selective nitrosation of a specified nitrogen atom of the urea is of utmost importance, for example, in the case of an unsymmetrically substituted homolog of BCNU, the nitrosation of the nitrogen atom which carries the 2-chloroethyl group. Studies of nitrosation in undiluted formic acid (Johnston et al, J. Med. Chem. 9, 892 to 911, 1966) have shown that the formation of 1-(2-chloroethyl)-1-nitroso urea is favored only in those cases where the geometry of the substituent in the 3-position provides steric control and directs the nitroso group into the desired position. The selective nitrosation fails when this steric control is not present.

I have now surprisingly found that the selective nitrosation can be achieved simply and completely, if an N-substituted alkyl-N-nitrosocarbamoyl azide, desirably an N-haloalkyl-N-nitroso carbamoyl azide, is used for the preparation of disubstituted nitroso ureas. Particularly useful are N-(2-haloethyl)-N-nitrosocarbamoyl azides, preferably N-(2-chloroethyl)-N-nitrosocarbamoyl azide, advantageously the 2-fluoroethyl, 2-bromoethyl and 2-iodoethyl compounds.

My U.S. Pat. No. 4,150,146, issued on Apr. 17, 1979, is concerned with a process for the preparation of 1,3-nitrosocarbamoyl azide is reacted, preferably at about 0° C., with an amine, a diamine, an aminoalcohol, an aminoacid or an aminoacid derivative to form the 1,3-disubstituted nitroso urea, the reaction being carried out in a solvent which is inert to the reactants under the reaction conditions. In the above alkyl compounds, the alkyl group may have from two to six carbon atoms and may be straight chained or branched or may be an unsubstituted cycloalkyl group or a cycloalkyl group substituted with an alkyl group having from one to four carbon atoms.

The hydrocarbon portion of the above amino compounds is an alkyl group, preferably having from two to six carbon atoms, advantageously from two to four carbon atoms, a cycloalkyl group, especially a cyclohexyl group, a cycloalkyl group substituted with an alkyl group, preferably having from one to four carbon atoms, or with one or more hydroxyl, halo or nitro groups, an unsubstituted phenyl, biphenyl or naphthyl group, or a phenyl, biphenyl or naphthyl group substituted with one or more lower alkyl, hydroxyl, halo or nitro groups. The aminoacid derivative may be an aminoacid ester or an aminoacid amide.

My present invention is concerned with a process for the preparation of N-substituted alkyl-N-nitrosocarbamoyl azides by reacting the corresponding alkylcarbamoyl azide with nitrogen tetroxide in the cold, preferably at 0° C., in which the alkyl group of the alkyl compounds is defined as above. The preferred alkylcarbamoyl azide is a haloalkylcarbamoyl azide, particularly the 2-chloroalkyl and the 2-fluoroalkyl compounds, most particularly the 2-chloroethyl and the 2-fluoroethyl compounds.

The alkylcarbamoyl azide is prepared in one step and without the use of pyridine by reacting the corresponding isocyanate with an alkali metal azide, particularly sodium azide, especially activated sodium azide, preferably at about 0° C.

The invention makes it possible to prepare a large number of unsymmetrically 1,3-disubstituted nitroso ureas and nitroso ureido compounds, which could not hitherto be prepared by methods known in the art or could only be prepared with a very inferior yield. It is therefore preferable to the process known from Helv. Chim. Acta, vol. 52, fasc. 8, 1969 and vol. 57, fasc. 8, 1974, No. 289 which prepares first the chloride and then the azide and must make use of pyridine, and to other conventional processes in which the urea structure is first obtained and is then nitrosated.

The N-nitrosation of the alkylcarbamoyl azides, for example the 2-chloroethylcarbamoyl azide, has proved that the nitroso group is attached in the required position. The subsequent aminolysis of the nitrosated carbamoylating agent gives alkyl-N-nitrosoureas, for example the 2-chloroethyl-N-nitroso urea, which are free of isomers.

It has been found that certain unsymmetrically 1,3-disubstituted nitroso ureas analogs of BCNU, disclosed and claimed in my U.S. Pat. No. 4,150,146, and prepared from the compounds of this invention, show higher anti-tumor activity, alone or in combination with other compounds, while posessing improved solubility in water or in tissue fluids and also have a lesser delayed toxicity than BCNU.

The invention will now be described by way of example with reference to the N-(2-chloroethyl)-N-nitrosocarbamoyl compound to illustrate the use in the synthesis of various Haloalkyl compounds. However, the invention is not to be limited thereby except as defined in the attached claims. The chemical compounds and the solvents used in the Examples were of synthesis grade or chemically pure. Nitrogen tetroxide was used in the form available in the trade, obtained from BASF, Ludwigshafen, Germany.

EXAMPLE 1

Preparation of 2-chloroethylcarbamoyl azide (I)

A solution of 2-chloroethyl isocyanate (0.2 mole) in 100 ml of benzene was slowly added to a stirred solution of activated sodium azide (0.2 mole) in 100 ml of hydrochloric acid (13%) maintained at 0° C. The two-phase reaction mixture was stirred for 4 hours at 0° C. and the water phase was removed. 2-chloroethylcarbamoyl azide was crystallized from benzene/petroleum ether in the form of white needles. Yield: 88%. M.P. 49.6° to 50.2° C. NMR(CDCl$_3$-TMS) $\delta = 3.4$ to 3.9 ppm (unres., 4H,CH$^2$—CH$^2$Cl); 6.12 ppm (br, s, iH, NH); MS(14 v): m/e 148 (M+), m/e 106(M-N$_3$)+, m/e 105 (M-HN$_3$)+ =base peak. An intensity ratio of m/e 148 / m/e 150 is typical for a monochlorinated compound.

EXAMPLE 2

Preparation of N-(2-chloroethyl)-N-nitrosocarbamoyl azide (II)

Nitrogen tetroxide (0,3 mole) was slowly added to a suspension of anhydrous sodium acetate (0.6 mole) in 300 ml of carbon tetrachloride at $-10°$ C. After warming to 0° C., 2-chloroethylcarbamoyl azide (0.2) was slowly added with a spatula to the stirred suspension. A white precipitate was formed (AcOH). After 15 minutes, the reaction mixture was poured into ice water. The separated organic phase was extracted twice with 50 ml of a cold solution of NaHCO$_3$ (1 molar) and was then washed neutral with 2×50 ml of ice cold water saturated with NaCl. It was then dried over anhydrous sodium sulfate. No attempt was made to isolate N-(chloroethyl)-N-nitrosocarbamoyl azide as it is potentially explosive. The NMR spectroscopic examination of the CCl$_4$ solution (internal standard TMS) showed the complete absence of an NH- signal and showed a pattern which is typical for the A$_2$B$_2$ system of the nitrosated 2-chloroethylamino group. $\delta = 3.50$ ppm (t, 2H, —CH$_2$—N—NO); 4.15 ppm (t, 2H, Cl—CH$_2$—).

The solution should be stored as cold as possible, for example deep-freezed, as it turns out that on standing at room temperature the Upfield pseudotriplet appears, having the center at $\delta = 4.87$ ppm. While I do not wish to bound by this theory, I believe that spectral change, which in one case took 48 hours, may possibly be ascribed to a thermally induced rearrangement of the compound, which possibly leads through the migration of the 1,3-acyl to the diazoester of azidocarbonic acid. If the solution is maintained at $-30°$ C., no such phenomenon takes place.

The reaction described in Examples 1 and 2 can also be carried out with the corresponding 2-fluoro, 2-bromo or 2-iodo compounds.

The following Examples show the use of N-(2-chloroethyl)-N-nitrosocarbamoyl azide for the preparation of various disubstituted 2-nitroso ureas.

EXAMPLE 3

Preparation of 1,1'-(polymethylene)-bis-3-(2-chloroethyl)-3-nitroso ureas (Compounds 1 to 5 of Table I)

Some 0.2 mole of N-(2-chloroethyl)-N-nitrosocarbamoyl azide in CCl$_4$ was diluted with an equal volume (150 ml) of cold (0° C.) n-pentane. (The yield of N-nitrosocarbamoyl azide from the nitrosation of the carbamoyl azide was taken as quantitative). Ethylene diamine (0.2 mole), dissolved in cold CCl$_4$/n-pentane was added dropwise to the stirred solution in an ice bath. After 3 hours, the the yellow precipitate formed was removed by suction and washed several times with benzene/pentane (1:1). It was then dissolved in acetone and the acetone solution poured into a tenfold volume of ice cold 0.1 N H$_2$SO$_4$. The precipitate was filtered off and again dissolved in acetone. The acetone solution was poured into a tenfold volume of water and the precipitate obtained again filtered off. This procedure was repeated until the wash water was neutral. After drying in a vacuum dessicator over CaCl$_2$, the nitroso urea was crystallized from methyl formate/isopropanol (1:1).

The process of this Example was repeated substituting ethylene diamine by propylene diamine to prepare Compound 2 of Table I, by tetramethylene diamine to prepare Compound 3, by pentamethylene diamine to prepare Compound 4, and by hexamethylene diamine to prepare Compound 5. The physical data for Compounds 1 to 5 are given in Table I.

EXAMPLE 4

Preparation of 1-($\alpha$-hydroxyalkyl)-3-(chloroethyl)-3-nitroso ureas (Compounds 6 to 8 of Table I)

A solution of some 0.2 mole of N-(chloroethyl)-N-nitrosocarbamoyl azide in CCl$_4$ was diluted with 100 ml of cold isopropanol and the CCl$_4$ was removed under vacuum at 0° C. Thereafter, 0.3 mole of $\beta$-aminoethanol, dissolved in 50 ml of isopropanol, was added dropwise to the isopropanol solution at $-5°$ C. while stirring. The reaction was allowed to proceed until no unreacted N-(2-chloroethyl)-N-nitrosocarbamoyl azide could be detected by TLC. This required 4 hours for 1-(2-hydroxyethyl)-3-(2-chloroethyl)-3-nitroso urea (Compound 6). When the reaction was completed, an equal volume of cold 1 N H$_2$SO$_4$ was added and the acid solution was extracted with ethyl formate. The ethyl formate phase was washed neutral with water and the washings were re-extracted. The combined organic phases were dried over Na$_2$SO$_4$ and concentrated. The pure Compound 6 was crystallized in the form of light yellow needles from ethyl formate/n-pentane in a deep-freezer and then dried under vacuum.

The process of this Example was repeated substituting $\beta$-aminoethanol by $\gamma$-aminopropanol to prepare Compound 7, and by $\delta$-amino-n-butanol to prepare Coumpound 8. The reaction to prepare Compound 7 took 12 hours to completion. Compounds 7 and 8 could not be crystallized. They were purified by column chromatography on silica gel (solvent composition: acetone/n-pentane/benzene 1:1:1). After the removal of the solvent at 0° C. under vacuum, these liquid nitroso ureas were freeze dried at $-10°$ C. (24 hours).

The following Example illustrates the preparation of esters of 1-($\omega$-hydroxyalkyl-3-(2-chloroethyl)-3-nitroso ureas.

EXAMPLE 5

Preparation of a methanesulfonic acid ester of 1-(2-hydroxyethyl)-3-nitroso urea (Compound 9 of Table I)

0.06 mole of 1-(2-hydroxyethyl)-3-(2-chloroethyl)-3-nitroso urea was dissolved in 50 ml of pyridine, freshly distilled over KOH. 0.13 mole of methanesulfonyl chloride in 40 ml of pyridine was then added dropwise over 3 hours. The reaction charge was then left overnight at 0° C. 60 ml of ice water was then added with cooling, the temperature brought down to −10° C. and the mixture was slowly acidified with concentrated HCl. It was then shaken with ethyl formate, the ethyl formate was dried over Na$_2$SO$_4$, concentrated and an equal volume of n-pentane was added. The methanesulfonic acid ester crystallized in a deep freezer at −18° C. and was recrystallized from ethyl formate/n-pentane. The substance was shown by TLC to be pure; the results of the elementary analysis were within ±0.4% of theory. Molar absorption in the UV region, typical infrared absorptions and the NMR spectrum confirmed the purity and the stucture. Yield: 73%; MP: 59°–61° C.

This compound is of special interest as it is built of the molecule halves of two cytostatically active substances, viz, BCNU and 1,4-bis-(methanesulfonyloxy)-butane of the formula (CH$_3$—SO$_2$—O—CH$_2$—CH$_2$)$_2$ ("Myleran").

Animal test results have shown excellent activity against rat autochthonic DMBA-induced mammary carcinoma, significantly exceeding that of "Adriamycin" (Reg.TM) which is a much used chemotherapeutic agent.

The following Example illustrates the preparation of a 3-nitrosoureido aminoacid amide by reacting an N-(substituted alkyl) N-nitrosocarbamoyl azide with an aminoacid amide.

EXAMPLE 6

Preparation of 2-(3-(2-chloroethyl))-3-nitrosoureido acetamide (Compound 10 of Table I)

A solution of 0.3 mole of glycinamide hydrochloride was brought to pH 9 with KOH and was added dropwise to an ice cold stirred solution of 0.2 mole of N-(2-chloroethyl)-N-nitrosocarbamoyl azide in 150 ml of isopropanol. The reaction proceeded quickly (in about 1 hour). When TLC showed no unreacted N-(2-chloroethyl)-N-nitrosocarbamoyl azide, it was acidified with 1 N H$_2$SO$_4$ and extracted with ethyl formate. The organic phase was washed neutral and dried over Na$_2$SO$_4$. The nitrosoureido compound was separated from its impurities by several fractional crystallizations from ethyl formate and was finally recrystallized from ethanol. TLC showed the substance to be pure. The NMR spectrum and the elementary analysis showed the presence of a half molecule of water of crystallization. UV and infrared spectroscopy confirmed the purity and the structure. Yield: 40%; MP (0° C.): 114.2°–114.5° C.

Preliminary animal test results have shown that the above prepared Compound 10 has the same activity against S. C. Walker carcinosarcoma as BCNU. However, it is easier to apply than BCNU because of its better solubility in water. As well as that, and contrary to BCNU, it appears to have little delayed toxicity. Compound 10 also shows better activity than "Adriamycin" or BCNU against autochthonic DMBA-induced mammary rat carcinoma.

When glycine is used in the above preparation in place of glycinamide hydrochloride, 2(3-(2-chloroethyl))-3-nitrosoureido acetic acid is obtained, which may then be converted into its salt, particularly an alkali metal salt.

When a glycine ester is used in the above preparation in place of glycinamide hydrochloride, the reaction leads to the preparation of the corresponding 2-(3-(2-chloroethyl))-3-nitrosoureido acetic acid ester.

The sequence of chemical reaction steps in the preparation of Compounds 1 to 10 can be shown schematically as follows:

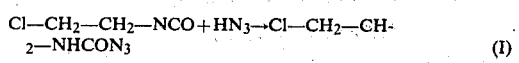
(I)

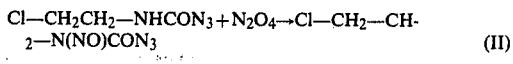
(II)

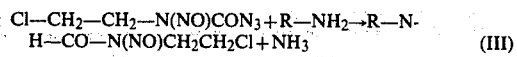
(III)

For Compounds 1 to 5, R represents the polymethylene group of 2 to 6 carbon atoms. For Compounds 6 to 7, R represents the ω-hydroxyalkyl residue of 2 to 4 carbon atoms. For Compound 9, R represents a 2-methanesulfonyloxyethyl residue and for Compound 10 an acetamide residue. Physical data for Compounds 1 to 10 are given in the accompanying Table I.

All the compounds synthesized were found by thin leaf chromatography (TLC) (silica gel leaves, solvents acetone/n-pentane benzene 1:1:1) to be pure.

The results of the elementary analysis were within ±0.4% of theory, with the exception of the liquid compounds 7 and 8 which were not stable enough for elementary analysis. However, also for these compounds the molar absorption in the UV region and the typical infrared absorption of the N-nitrosoureido group were in agreement with data known for other N-mitroso ureas. Also the NMR spectrum confirmed the structure and the purity of the compounds.

The chemotherapeutic activity of Compounds 1 to 8 against rat leukaemia L 5222 and S. C. Walker carcinosarcoma is shown in the accompanying Table II, together with that of still another BCNU analog and of BCNU itself. Compound 6 is shown to have outstanding activity.

Numerous modifications and variations of my invention are possible in the light of the above teachings and, therefore, within the scope of the appended claims, my invention may be practised other than as particularly described.

TABLE I

Physical properties of 2-chloroethyl-N-nitroso ureas

| Compound (CNU is 3-(2-chloroethyl)-3-nitroso urea of the formula —NHCON(NO)CH$_2$CH$_2$Cl) | Mp(°0) n$_D^{20}$ | Yield (%) |
|---|---|---|
| 1. 1,1'-ethylenebis-CNU—(CH$_2$)$_2$—CNU | 129.9–130.9 (dec.) | 35 |
| 2. 1,1'-propylenebis-CNU—(CH$_2$)$_3$—CNU | 69.2–72.1 (dec.) | 35 |
| 3. 1,1'-tetramethylenebis-CNU—(CH$_2$)$_4$—CNU | 104.5–106.1 (dec.) | 37 |
| 4. 1,1'-pentamethylenebis-CNU—(CH$_2$)$_5$—CNU | 96.0–98.0 (dec.) | 39 |
| 5. 1,1'-hexamethylenebis-CNU—(CH$_2$)$_6$—CNU | 84.0–86.0 (dec.) | 46 |
| 6. 1-(2-hydroxyethyl)-CNU—CH$_2$—CH$_2$OH | 56.0–58.0 (dec.) | 49 |
| 7. 1-(3-hydroxypropyl)-CNU—(CH$_2$)$_2$—CH$_2$OH | n$_D^{20}$ = 1.4655 | 47 |
| 8. 1-(4-hydroxybutyl)-CNU—(CH$_2$)$_3$—CH$_2$OH | n$_D^{20}$ = 1.4855 | 47 |
| 9. 1-(2-methanesulfonyloxy)-ethyl)-3-(2-chloroethyl)-3-nitroso urea (CNU—CH$_2$CH$_2$OSO$_2$—CH$_3$) | 59–61 | 73 |
| 10. 2-(3-chloroethyl)- | | |

TABLE I-continued

Physical properties of 2-chloroethyl-N-nitroso ureas

| Compound (CNU is 3-(2-chloroethyl)-3-nitroso urea of the formula —NHCON(NO)CH$_2$CH$_2$Cl) | Mp(°0) n$_D^{20}$ | Yield (%) |
|---|---|---|
| 3-nitrosoureido acetamide | 114.2–114.5 | 40 |

TABLE II

The chemotherapeutic activity of Compounds 1 to 8, another analog of BCNU, and BCNU against rat leukaemia L 5222 and s.c. Walker carcinosarcoma

| Compound[1] | L 5222[2] cures %[3] | s.c. Walker[4] T.W.I. %[5] |
|---|---|---|
| BCNU | 70 | 83 |
| 1 | 60 | 75 |
| 2 | 60 | 72 |
| 3 | 75 | 77 |
| 4 | 30 | 68 |
| 5 | 50 | 70 |
| 6 | 90 | 85 |
| 7 | 10 | 0 |
| 8 | 5 | 4 |
| 1,1′-(4-methyl-m-phenylene)bis-CNU | 0 | 35 |

[1] 50% of the acute LD$_{50}$ were given i.p.
[2] Treatment on day 6 after transplantation of 5 × 10$^6$ cells.
[3] Rats surviving 60 days after treatment were considered cured.
[4] Treatment on day 4 after transplantation. Each group consisted of 10 Sprague Dawley rats.
[5] T.W.I. corresponds to tumor weight inhibition in % on day 8, calculated by the formula $$\frac{\text{control} - \text{treated}}{\text{control}} \times 100$$

What I claim is:
1. N-haloalkyl-N-nitrosocarbamoyl azide.
2. N-(2-chloroethyl)-N-nitrosocarbamoyl azide.
3. N-halo-C$_2$-C$_6$-alkyl-N-nitrosocarbamoyl azide.
4. N-haloethyl-N-nitrosocarbamoyl azide.
5. N-(2-fluoroethyl)-N-nitrosocarbamoyl azide.
6. Process for the preparation of the compound claimed in claim 1, which comprises reacting a haloalkyl carbamoyl azide with nitrogen tetroxide in an inert solvent in the cold.
7. The process claimed in claim 6, wherein the haloalkyl carbamoyl azide has from two to six carbon atoms, whereby N-(halo-C$_2$-C$_6$alkyl)-N-nitrosocarbamoyl azide is formed.
8. The process claimed in claim 6, wherein the haloalkyl carbamoyl azide is 2-chloroethyl carbamoyl azide, whereby N-2-chloroethyl-N-nitrosocarbamoyl azide is formed.

* * * * *